(12) United States Patent
Williams

(10) Patent No.: US 9,066,735 B2
(45) Date of Patent: Jun. 30, 2015

(54) ELECTROSURGICAL SYSTEM

(71) Applicant: GYRUS MEDICAL LIMITED, Cardiff (GB)

(72) Inventor: David Nicholas Williams, Caerphilly (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 2 days.

(21) Appl. No.: 14/020,240

(22) Filed: Sep. 6, 2013

(65) Prior Publication Data

US 2014/0303612 A1 Oct. 9, 2014

(30) Foreign Application Priority Data

Apr. 3, 2013 (GB) .................................. 1305987.8

(51) Int. Cl.
*A61B 18/18* (2006.01)
*A61B 19/00* (2006.01)
*A61B 18/12* (2006.01)
*A61B 18/14* (2006.01)
*A61B 18/00* (2006.01)

(52) U.S. Cl.
CPC ................ *A61B 18/18* (2013.01); *A61B 19/46* (2013.01); *A61B 18/1206* (2013.01); *A61B 18/1402* (2013.01); *A61B 2018/00928* (2013.01); *A61B 2018/0094* (2013.01)

(58) Field of Classification Search
CPC ............ A61B 2018/00636; A61B 2018/0642; A61B 2018/00648; A61B 2018/00654; A61B 2018/00666; A61B 2018/00696; A61B 2018/00702; A61B 2018/00708; A61B 2018/00726; A61B 2018/00732; A61B 2018/00761; A61B 2018/00773; A61B 2018/00779; A61B 2018/00845; A61B 2018/00851; A61B 2018/00886; A61B 2018/0091; A61B 2018/1266; A61B 18/12; A61B 18/1206
USPC ....................................................... 606/32–35
See application file for complete search history.

(56) References Cited

U.S. PATENT DOCUMENTS

| 6,074,386 A * | 6/2000 | Goble et al. ..................... 606/34 |
| 2004/0054365 A1 * | 3/2004 | Goble .............................. 606/34 |
| 2008/0294157 A1 * | 11/2008 | Hosier ............................ 606/34 |

FOREIGN PATENT DOCUMENTS

| EP | 2 108 325 A1 | 10/2009 |
| WO | WO 2008/142398 A1 | 11/2008 |

OTHER PUBLICATIONS

Search Report issued in British Patent Application No. 1305987.8 dated Sep. 20, 2013.
International Search Report issued in United Kingdom Patent Application No. GB1318618.4 dated May 14, 2014.
International Search Report and Written Opinion mailed Jun. 2, 2014 issued in International Patent Application No. PCT/GB2014/051034.

\* cited by examiner

*Primary Examiner* — Joseph Stoklosa
*Assistant Examiner* — Amanda Zink
(74) *Attorney, Agent, or Firm* — Oliff PLC

(57) ABSTRACT

An electrosurgical system includes at least a first unit and a second unit, the second unit being detachably connectible to the first unit and including an electrode assembly. The first unit includes a power supply, an RF oscillator circuit for generating a radio frequency output, and an output stage adapted to supply an RE output to the electrode assembly. The second unit includes an identification circuit presenting, in an alternating manner, a parameter with a first finite non-zero value for a first time period, and a parameter with a second finite value for a second time period. The first unit includes a sensing circuit and a controller adapted to detect a characteristic of the identification circuit and provide an output signal, the controller connected to the sensing circuit and receiving the output signal, adjusts the RF output so as to suit the particular electrode assembly.

16 Claims, 5 Drawing Sheets

ELECTROSURGICAL SYSTEM

TECHNICAL FIELD

This invention relates to an electrosurgical system for use in the treatment of tissue. Such systems are used in endoscopic or "keyhole" surgery, as well as more traditional "open" surgery.

BACKGROUND TO THE INVENTION

Many electrosurgical systems have some form of identification system, such that when an electrosurgical instrument is connected to an electrosurgical generator, the generator is able to detect which type of instrument is present, and even use settings such as power and voltage settings which are appropriate for that particular instrument or type of instrument. Our U.S. Pat. No. 6,074,386 is one example of such an identification system, although other types are also known.

SUMMARY OF THE INVENTION

Embodiments of the present invention attempt to provide an alternative to such identification systems, with increased complexity so as to make it more difficult for non-authorised instruments to be used. Accordingly, from one aspect an electrosurgical system is provided comprising at least a first unit and a second unit, the second unit being detachably connectible to the first unit and being associated with an electrode assembly, the first unit comprising:

a) a power supply, b) an RF oscillator circuit for generating a radio frequency output, c) an output stage adapted to supply an RF output to the electrode assembly, the second unit comprising an identification circuit presenting to the first unit, in an alternating manner, a parameter with a first finite non-zero value for a first time period, and a parameter with a second finite value for a second time period, the first unit including a sensing circuit adapted to detect a characteristic of the identification circuit and provide an output signal, the first unit further including a controller connected to the sensing circuit and receiving the output signal, the controller being configured to adjust the RF output in response to the output signal from the sensing circuit so as to suit the particular electrode assembly.

The first unit conveniently comprises an electrosurgical generator, and the second unit comprises an electrosurgical instrument detachably connected to the generator, typically by means of a cable and a connector. The electrosurgical instrument conveniently integrally includes the electrode assembly, in a "one piece" configuration. Alternatively, the electrosurgical instrument comprises a handpiece and a separate electrode assembly which is selectively attached and detached with respect to the handpiece, a so-called "two piece" configuration. The reference above to the second unit being "associated with" an electrode assembly is specifically intended to include both of these arrangements, and also a further arrangement in which the second unit comprises an adaptor unit, connected in between the electrosurgical instrument and the electrosurgical generator.

In a further alternative arrangement, the first unit comprises a handheld electrosurgical handpiece, and the second unit comprises an electrode unit detachably connected to the electrosurgical handpiece. Conveniently, the electrode unit comprises an elongate shaft having the electrode assembly at one end of the shaft and a connector at the other end of the shaft, for connecting the electrode unit to the handpiece. Whichever arrangement is employed, the sensing circuit within the first unit helps to identify the electrode assembly in question and sends an output signal to the controller, which in turn adjusts the RF output to suit the particular electrode assembly.

According to one convenient arrangement, the first unit is adapted to detect the frequency of alternating between the first time period and the second time period. Alternatively, the first unit is adapted to detect the ratio between the first time period and the second time period. According to a further alternative arrangement, the first unit is adapted to detect the difference between the value of the parameter during the first and second time periods. Whichever arrangement is used, the characteristic used to identify the second unit to the first unit is a dynamic one, based on the alternating between the first and second values. This added complexity makes the identification harder to duplicate, and ensures that only known suitable electrode assemblies are able to be used in connection with the first unit.

It is common for several generations of electrosurgical instrument to be used over the lifetime of an electrosurgical generator, or for a combination of first and second generation generators to be in the field at any one time. This means that some generators may be capable of detecting the dynamic identification characteristics, while other older versions are not. Thus, the first unit is conceivably adapted to detect the value of the parameter during the first time period, or the second time period, or both. In this way, those first units capable of detecting the dynamic identification characteristics can do so for added security, while those older versions incapable of detecting the dynamic identification characteristics can still be used in connection with second units exhibiting a dynamic identification characteristic, even though only the value of the parameter and not its changing characteristics is detected in such older versions.

For added sophistication, the first unit may detect a combination of the features detailed above, for example the value of the parameter during either the first or second time period together with the frequency at which the time periods alternate. Other combinations will be apparent to those skilled in the art such that each and every combination does not need to be listed here.

Within the above, where the first unit is adapted to detect a value of the parameter, or a difference therein, or a ratio of time periods, or frequency of alternating between time periods, etc, as described above, in a preferred embodiment it is a combination of the the sensing circuit and the controller that make the final identification of the second unit that has been connected to the first unit. Specifically, the sensing circuit may output a sensing signal indicative of the parameter, difference, ration, frequency, etc. the sensing signal then being interpreted by the controller to make the identification and then preferably control the first unit appropriately.

In a preferred arrangement, the identification circuit includes at least first and second passive electrical identification components having a parameter of a finite non-zero value, the value of the first identification component being different from the value of the second identification component. The identification circuit conveniently also includes switching means for switching between first and second combinations of the first and second identification components. In one arrangement, the switching means switches between a first combination of solely the first identification component and a second combination of solely the second identification component. In an alternative arrangement, the switching means switches between a first combination of solely the first identification component and a second combination of both the first and second identification components. Whichever arrangement is employed, as the values of the parameter are different between the first and second identification components, the result is a repeating high/low/high/low value for the parameter. This alternating value is sensed by the sensing circuit within the first unit, in order for the first unit to identify the second unit and set appropriate output characteristics.

Preferably, the parameter with the first and second finite values is capacitance, such that the first and second identification components are capacitors. Our U.S. Pat. No. 6,074, 386 describes how the value of the capacitor can be established by setting up a resonant circuit between the first and second units, and detecting the resonant frequency of such a resonant circuit. This method, or alternatives readily known to those skilled in the art, may be employed for sensing the capacitances associated with the dynamic identification circuit within the second unit.

Conveniently, the switching means comprises a transistor. However, other switching components are known to those skilled in the art, and the use of such switching components may depend on the sterilization method used to sterilize the second unit.

Another embodiment of the invention provides an electrosurgical instrument, or an electrode assembly for an electrosurgical instrument, comprising a connection interface and an identification circuit. The identification circuit is arranged to present at the connection interface a time-varying electrical parameter, the time-varying electrical parameter serving as an identification signature determinative of at least one property of the electrosurgical instrument or electrode assembly. The property may be for example the identity of the instrument or assembly, or one or more electrical characteristics or input signal requirements.

In one embodiment the identification circuit comprises a network of electrical components, and a switching device to switch one or more of the electrical components in and out of the network whereby to vary the electrical parameter. Preferably the network of electrical components comprises one or more reactive components, a resonant frequency of the network altering as the switching device switches the one or more reactive components in and out of the network.

In one specific embodiment the network comprises at least two reactive components arranged in parallel, the switching device, preferably being a transistor, being arranged to switch periodically one of the components in and out of the network, whereby the time-varying electrical parameter switches between a larger and smaller reactance or impedance. In some embodiments of the invention, the reactive components are conveniently capacitors.

Another aspect of the invention provides a method of operating an electrosurgical system comprising at least a first unit and a second unit, the second unit being detachably connectible to the first unit and being associated with an electrode assembly, the first unit providing an RF output signal to the second unit, the method comprising: presenting from the second unit to the first unit, in a time-varying manner, a parameter with a first finite non-zero value for a first time period, and a parameter with a second finite value for a second time period, detecting the parameter in the first unit, and adjusting the RF output signal of the first unit in response to the parameter detection so as to suit the particular electrode assembly; wherein the time-varying nature of the parameter provides for identification of the particular electrode assembly.

DESCRIPTION OF THE DRAWINGS

The invention will now be described in more detail, by way of example only, with reference to the accompanying drawings, in which.

DESCRIPTION OF THE EMBODIMENTS

Figure 1:
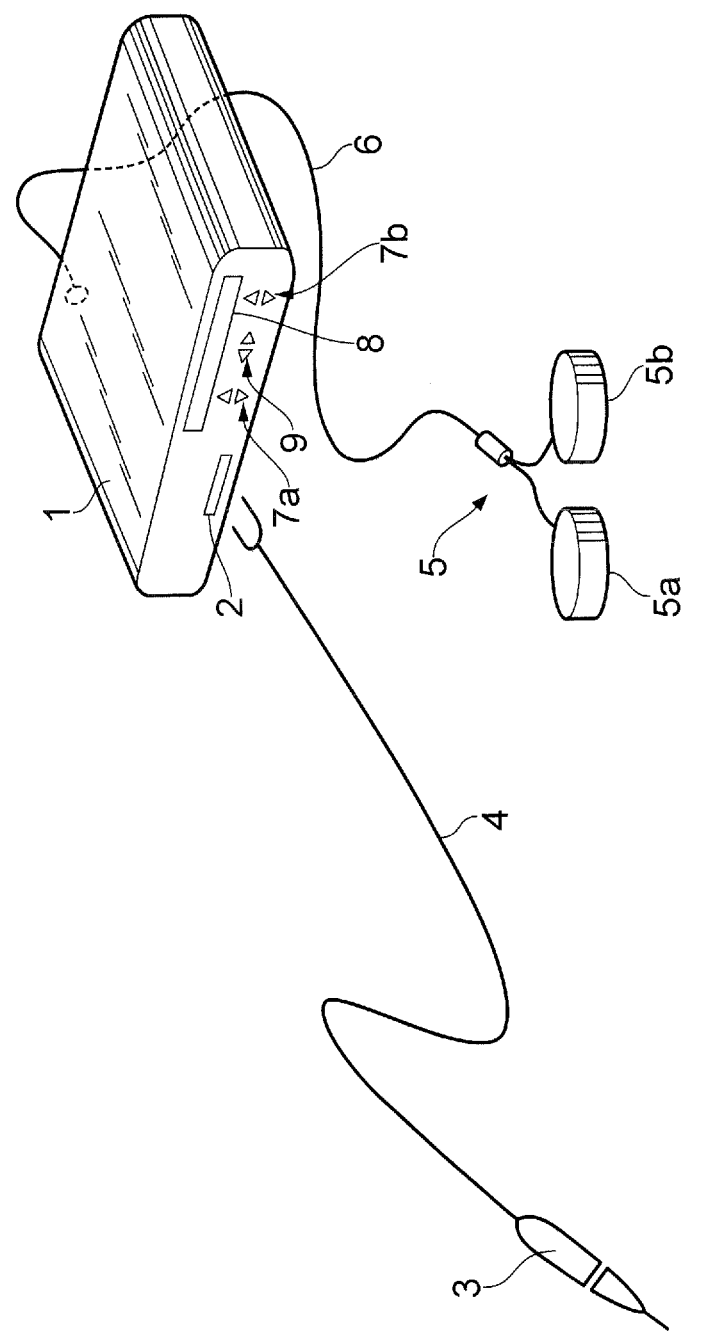
FIG. 1 is a schematic diagram of an electrosurgical system according to the present invention.

Referring to the drawings, FIG. 1 shows a conventional electrosurgical apparatus including a first unit in the form of a generator 1 having an output socket 2 providing a radio frequency (RF) output, for a second unit in the form of an instrument 3, via a connection cord 4. Activation of the generator 1 may be performed by means of a footswitch unit 5 connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9 are provided as an alternative means for selection between the desiccation and vaporisation modes.

Figure 2:
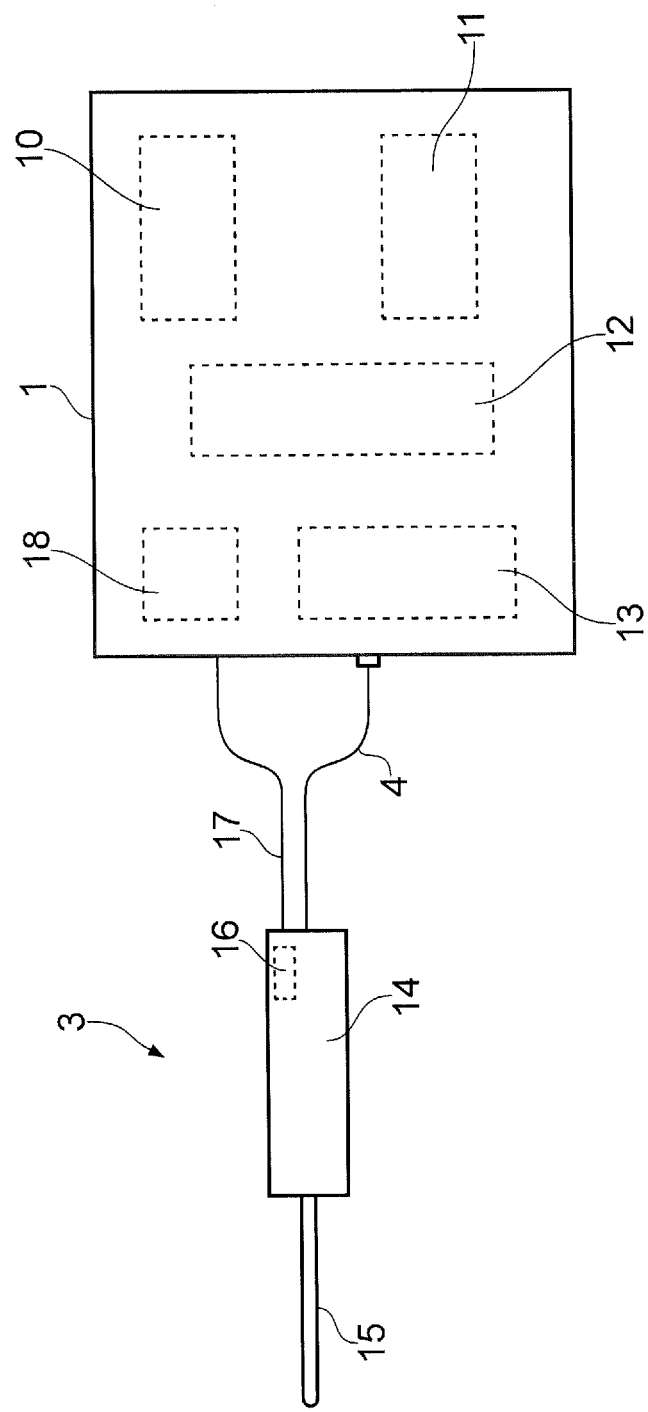
FIG. 2 is a schematic diagrams of the system of FIG. 1, showing various internal components.

FIG. 2 shows a schematic version of FIG. 1 showing some of the internal components of the generator 1 and instrument 3. The generator 1 includes a power supply 10, RF oscillator 11, and controller 12, all designed to provide an RF output to output stage 13. The instrument 3 includes a handpiece 14 and an electrode assembly 15. In some arrangements the electrode assembly 15 is detachable from the handpiece 14 so that the same handpiece can be used with different electrode assemblies. In other arrangements, the handpiece 14, electrode assembly 15 and connection cord 4 are all formed as a single one-piece assembly.

The instrument 3 also includes an identification circuit 16, which is associated with the electrode assembly 15 if the electrode assembly is detachable, or otherwise with the handpiece 14 if the instrument is a one-piece assembly. The identification circuit 16 is connected via additional line 17 to a sensing circuit 18 located within the generator 1.

Figure 3:
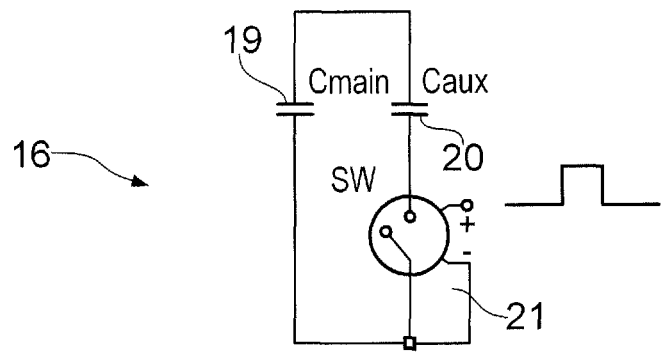
FIG. 3 is a schematic circuit diagram of an identification circuit used within the system of FIG. 1.

The identification circuit 16 will be further described with reference to FIG. 3. The circuit comprises first capacitor 19 (Cmain), second capacitor 20 (Caux) and a switching circuit 21. The switching circuit 21 alternates between connecting the second capacitor in and out of parallel with the first capacitor, so that the overall capacitance of the circuit is altered in dependence on the switching of the switching circuit. In particular, because the capacitances of capacitors connected in parallel add together, the operation of the switching circuit 21 causes the overall capacitance to switch between a lower capacitance Cmain, and a higher capacitance equal to the sum of Cmain and Caux. When the capacitances are connected into and form part of a resonant circuit with the sensing circuit in the generator, the switching in and out of Caux 21 by the switching circuit 21 will cause the resonant frequency of the whole resonant circuit to change. This change can be detected by circuitry in the generator, and the change used to identify the type of electrosurgical instrument or electrode assembly that is attached, as described further below.

More particularly, generally the frequency of oscillation of a resonant circuit will be given by the formula below;

$$Fo = \frac{1}{2\pi\sqrt{(LC)}}$$

Hence, as Caux is switched into the circuit by switch 21, the resonant frequency Fo of the resonant circuit will decrease. Detecting changes in the frequency of oscillation therefore gives an indication of the value of the capacitor 20, and for a known inductance the values of both Cmain and Caux can be found by monitoring the resonant frequency thus obtained. As described further below, the sensing circuit 18 contains an oscillator that oscillates at different frequencies, and the controller 12 detects the frequency of oscillation, both when the first capacitor is connected to the sensing circuit and also when the second capacitor is connected to the sensing circuit. Thus the sensing circuit 18 and controller 12 are hence able to identify the type of handpiece 14 and hence electrode assembly 15 connected to the generator 1. The controller 12 accordingly adjusts the power supply 10 and/or oscillator 11 to supply an RF output to the output stage 13 which is suitable for the particular electrode assembly 15. When a different handpiece is connected to the generator 1, the sensing circuit 18 will oscillate at a different frequency of oscillation caused by the impedances in the identification circuit 16, and hence the controller will arrange for a different RF output, more suitable for the electrode assembly associated with that particular handpiece.

Figure 4:
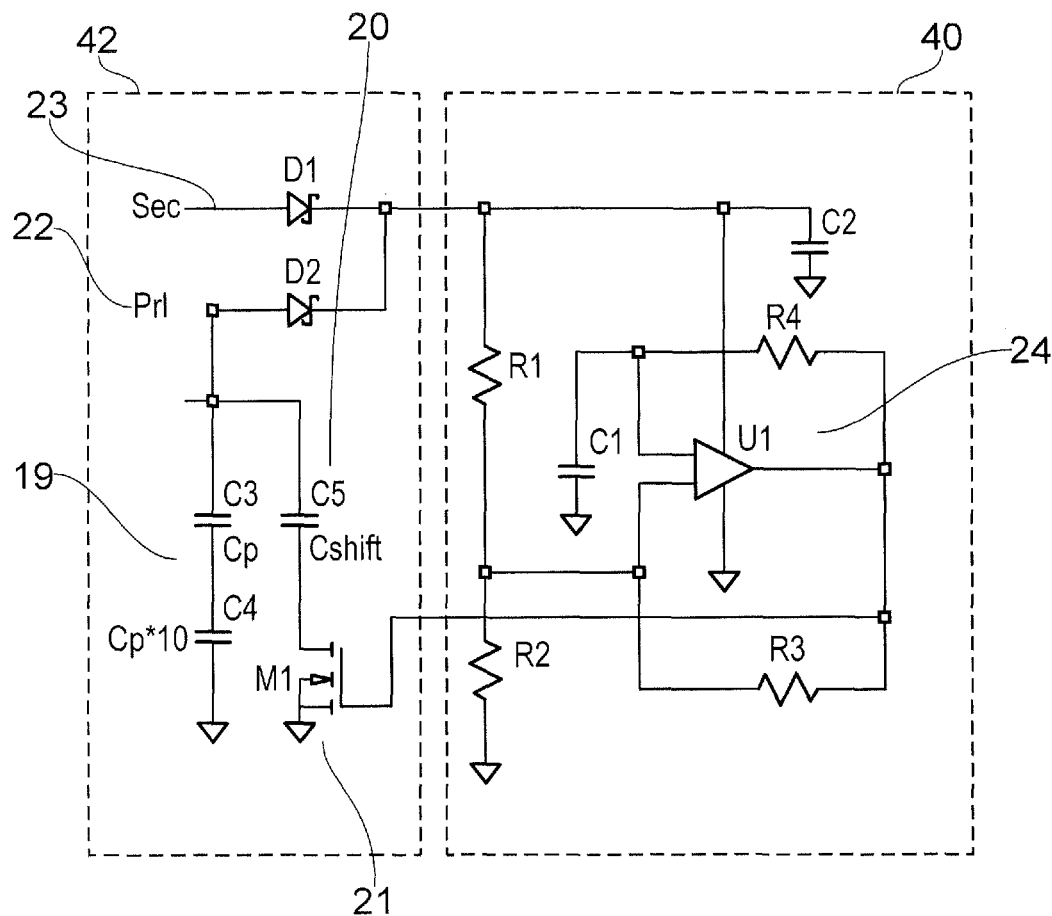
FIG. 4 is a more detailed circuit diagram of the identification circuit of FIG. 3.

FIG. 4 shows a detailed circuit diagram for the identification circuit 16. The identification comprises a reactive output stage 42, and a switch control oscillator circuit 40. The reactive output stage in this circuit is capacitive in nature, and comprises two capacitors $C_3$ and $C_4$ in series (together the equivalent of the first capacitor 19 (Cmain) of FIG. 3), the value of $C_4$ typically being of the order of 10 times the value of $C_3$. A second capacitor 20 (the equivalent of Caux) is designated $C_5$, and a transistor $M_1$ switches the second capacitor 20 in and out of the reactive output stage 42, and more specifically in and out of being connected in parallel with capacitors $C_3$ and $C_4$. Primary and secondary lines 22 & 23 provide power for the transistor $M_1$, and also for the switch control oscillator circuit 40. The switch control oscillator circuit 40 comprises an op-amp 24 configured as an oscillator, which produces a square wave output which is fed to the gate of transistor M1 as a switching signal. The frequency of the square wave output is set to an appropriate frequency (which may be in the range of a few Hz to a few hundred Hz) by the oscillator biasing circuitry C1, R1, R2, R3, and R4. The square wave output from the oscillator drives the transistor M1 in and out of saturation in order to switch the capacitor C5 in and out of the circuit of the reactive output stage 42.

When the transistor $M_1$ is not conducting, the total value of C that would be seen at the primary input 21 is $$\frac{C3 \cdot C4}{C3 + C4}$$

whereas when the transistor $M_1$ is conducting, the value of C that would be seen is $$\frac{C3 \cdot C4}{C3 + C4} + C5.$$

This means that the frequency of oscillation will be lower when the transistor is conducting as compared with the time when the transistor is not conducting. The controller 12 monitors the frequency of oscillation of the resonant circuit in the sensing circuit 18 (described further below) during the time when the transistor $M_1$ is conducting, and also during the time when the transistor $M_1$ is not conducting. In this way, the sensing circuit 18 and controller 12 determine the values of the capacitors $C_3$, $C_4$ & $C_5$, and hence identify the type of instrument 3 connected to the generator 1.

The identification circuit 16 therefore provides multiple parameters that may be altered to provide different identifications. In particular, the values of $C_3$, $C_4$ & $C_5$ may all be changed, which will give different resonant frequencies. The circuit arrangement provides for two resonant frequencies, Fo1 when C5 is switched out, and Fo2 when C5 is switched in, where Fo2 is less than Fo1. The values of $C_3$, $C_4$ & $C_5$ may be selected to give any desired resonant frequencies. Alternatively or additionally, the biasing circuitry of the oscillator circuit 24 may also be altered, to give a different oscillator frequency, and hence frequency of switching Fs between the two resonant frequencies. The circuit of FIG. 4 therefore provides three parameters (Fo1, Fo2, and Fs) that may be altered to provide an identification signature for the electrosurgical instrument, and many different combinations of these three parameters are possible, resulting in a large number of possible identification signatures.

Figure 6:
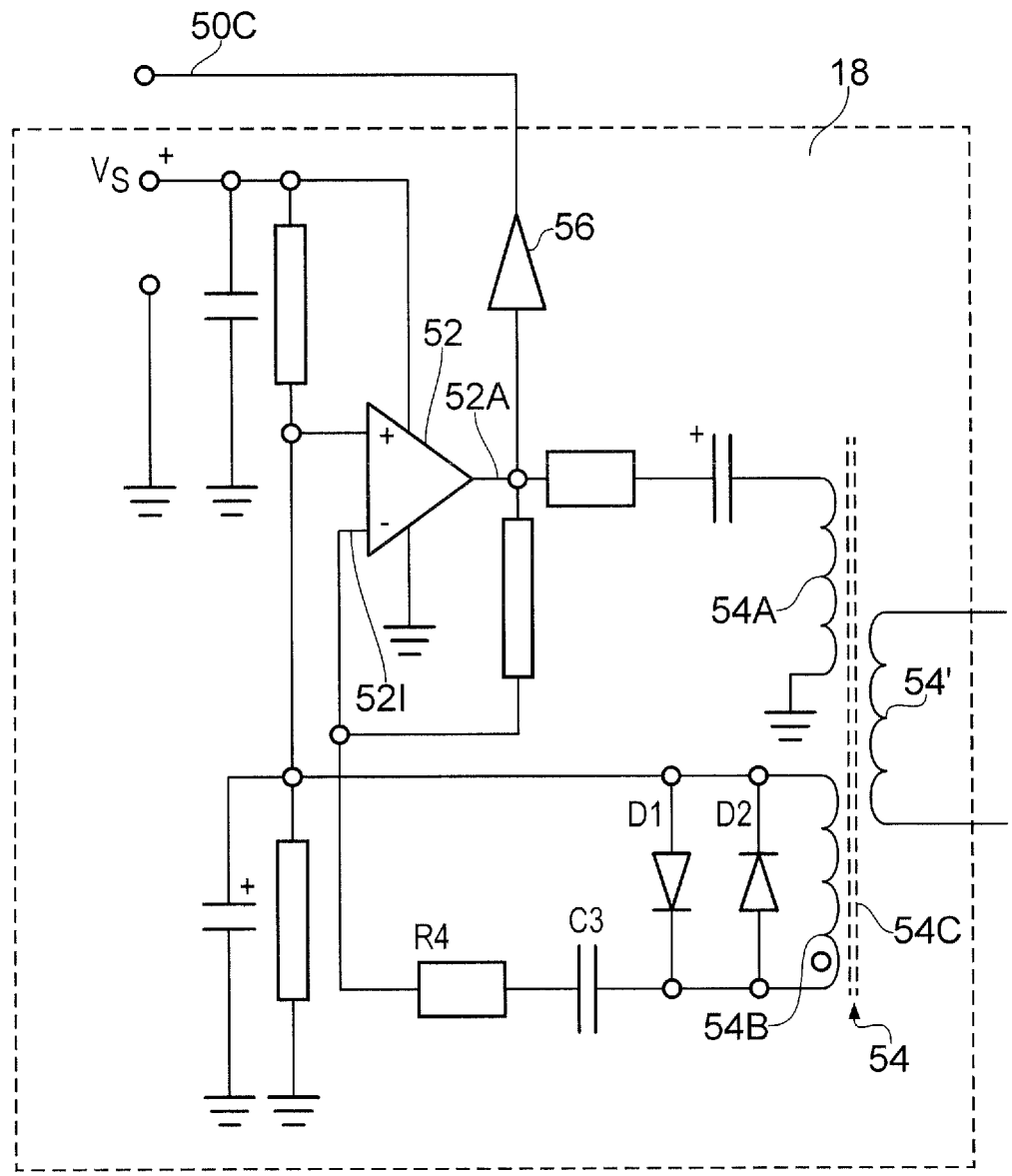
FIG. 6 is a circuit diagram of a sensing circuit that may be used in an embodiment of the invention.

In order to determine the above parameters, the sensing circuit 18 couples to the primary input 22. An example sensing circuit 18 is shown in FIG. 6, which is almost identical to the sensing circuit described in our prior U.S. Pat. No. 6,074,386. Here, sensing circuit 18 is centred on an operational amplifier 52 having a low impedance output 52A driving an excitation primary winding 54A of an isolation transformer 54. A secondary winding 54' of the transformer 54 is coupled between the primary input 22 of identification circuit and ground, so that winding 54' and capacitors 19 and 20 in the identification circuit 16 form a parallel resonant circuit. The resonant frequency of the resonant circuit is typically within the range of from 2 kHz to 150 kHz, depending on the value of capacitors C3, C4, and C5.

The transformer 54 also has a sense winding 54B coupled between an AC ground on one side and the inverting input 52I of the operational amplifier 52, thereby providing a feedback path from the transformer. Since winding 54B is effectively coupled to the excitation winding 54A via the resonant secondary winding 54', the presence of the resonant circuit largely filters out the harmonics of the square wave output of the operational amplifier 52.

Clamp diodes D1 and D2 connected with opposite pluralities across sense winding 54B provide, in conjunction with capacitor C3 and resistor R4, a phase shift network causing a 90 degree phase lag with respect to the excitation winding output.

The three windings 54A, 54B and 54' of transformer 54 are wound on a three-section bobbin with a central threaded iron dust core 54C, this material being chosen due to its high curie point and consequent minimal thermal drift. Alternatively, core 54C may be made of a ferrite material with a comparatively large A1 value in conjunction with a calibration reference to allow compensation for thermal drift by, for example, switching in a known capacitance across the resonant winding 54'.

Coupling between the resonant secondary winding 54' and the other windings 54A, 54B of the transformer 54 is comparatively low to limit radio frequency feedback. Typically, the leakage inductance is in the region of 3 mH.

It will be appreciated from the above that operational amplifier 52 acts as an oscillator, oscillating at the resonant frequency of the resonant circuit produced by secondary winding 54' and capacitors 19 and 20 (C3, C4, and C5). The output signal produced by the operational amplifier 52 is amplified in a buffer amplifier 56 and applied to output terminal 50C from where it is fed to the controller 12 (see FIG. 2). Controller 12 contains a counter for determining the frequencies of oscillation (or an equivalent measurement, as discussed further below) from which the identity of the electrode assembly is obtained.

As a safety feature the controller 12 includes means for determining from the output of the identification circuit 16 whether any electrode assembly is connected to the generator. In such an eventuality, the oscillation frequency of the circuit 50 is outside a predetermined range (in this embodiment it is higher than 150 kHz) and the adjusting means generates a signal indicative of no electrode assembly being connected and the supply of RF output power to the handpiece 12 is inhibited.

The sensing circuit 18 and controller 12 may monitor parameters other than the absolute values of the capacitors $C_3$, $C_4$ & $C_5$. The sensing circuit and controller may alternatively calculate the difference in values between two or more of the capacitors, or alternatively the oscillation frequency of the transistor $M_1$, Alternatively, the sensing circuit and controller may monitor the ratio of the periods during which the transistor $M_1$ is in each of its two alternating states. Whichever parameter is monitored, the sensing circuit 18 and controller are able to establish a unique identifying characteristic for the type of instrument connected to the generator, such that the controller 12 can ensure that an RF output suitable for the electrode assembly associated with that instrument is provided.

Figure 5:
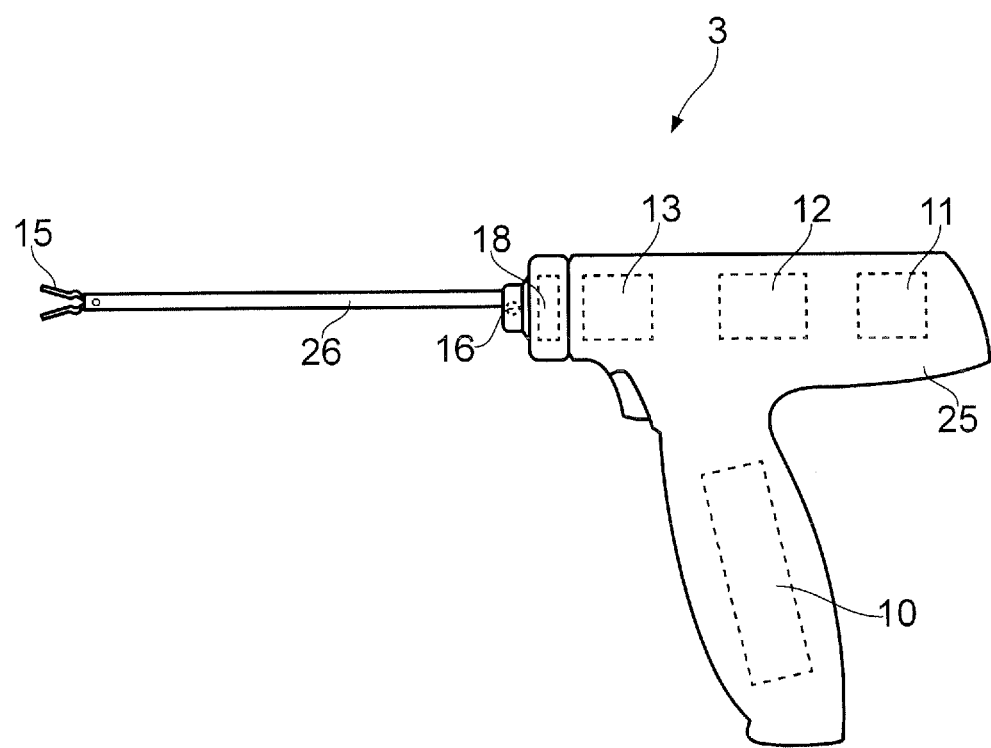
FIG. 5 is a schematic diagram of an alternative electrosurgical system according to the invention.

FIG. 5 shows an alternative type of system in which the generator 1 is provided within a handheld electrosurgical instrument. The instrument 3 is provided with a first unit in the form of a handle 25 within which the power supply 10, RF oscillator 11, controller 12, output stage 13 and sensing circuit 18 are located. Given that the instrument is handheld, the power supply 10 is typically a battery. A second unit in the form of a probe 26 is detachably connected to the handle 25, the probe including the identification circuit 16 and an electrode assembly 15. The identification circuit 16 and sensing circuit 18 cooperate as previously described to identify the type of probe connected to the handle 25, and hence the appropriate RF output to be supplied to the electrode assembly 18.

Variations from the above-described arrangements will be apparent to those skilled in the art without departing from the scope of the present invention. For example, greater sophistication is possible by the provision of more than two alternating values for the chosen parameter, conceivably three or even more. Whichever parameter is chosen and however many values are dynamically presented, the key feature of the invention is the provision of a dynamically varying parameter as opposed to a static value that remains constant in time. This dynamic variation in the value for the parameter being monitored allows for a degree of complexity sufficient to make it difficult for unauthorised instruments to duplicate the required signature and "fool" the generator or handheld instrument into accepting an unauthorised electrode assembly. In this way, the integrity of the electrosurgical system, and hence its efficiency and safety, is maintained to an extent greater than if unauthorised instruments are capable of being used without such controls.

The invention claimed is:

1. An electrosurgical system comprising:
    a first unit including:
        a) a power supply;
        b) an RF oscillator circuit for generating a radio frequency output; and
        c) an output stage adapted to supply an RF output to an electrode assembly; and
    a second unit detachably connectible to the first unit and being associated with the electrode assembly, the second unit including an identification circuit configured to present to the first unit whilst the second unit is connected to the first unit, in an alternating manner, a parameter with a first finite non-zero value for a first time period, and a parameter with a second finite value for a second time period;
    wherein the first unit further includes:
        d) a sensing circuit adapted to detect a characteristic of the identification circuit and provide an output signal; and
        e) a controller connected to the sensing circuit and configured to receive the output signal, the controller being configured to adjust the RF output in response to the output signal from the sensing circuit so as to suit the particular electrode assembly.

2. An electrosurgical system according to claim 1, wherein the first unit is adapted to detect a frequency of alternating between the first time period and the second time period.

3. An electrosurgical system according to claim 1, wherein the first unit is adapted to detect a ratio between the first time period and the second time period.

4. An electrosurgical system according to claim 1, wherein the first unit is adapted to detect a value of the parameter during the first time period.

5. An electrosurgical system according to claim 1, wherein the first unit is adapted to detect a value of the parameter during the second time period.

6. An electrosurgical system according to claim 1, wherein the first unit is adapted to detect a difference between a value of the parameter during the first time period and a value of the parameter during the second time period.

7. An electrosurgical system according to claim 1, wherein the identification circuit includes at least first and second passive electrical identification components having a parameter of a finite non-zero value, a value of the first identification component being different from a value of the second identification component.

8. An electrosurgical system according to claim 7, wherein the identification circuit also includes switching means for switching between first and second combinations of the first and second identification components.

9. An electrosurgical system according to claim 8, wherein the switching means switches between a first combination of solely the first identification component and a second combination of solely the second identification component.

10. An electrosurgical system according to claim 8, wherein the switching means switches between a first combination of solely the first identification component and a second combination of both the first and second identification components.

11. An electrosurgical system according to claim 8, wherein the switching means comprises a transistor.

12. An electrosurgical system according to claim 1, wherein the parameter with the first finite value and the parameter with the second finite value is reactance.

13. An electrosurgical system according to claim 12, wherein the first and second identification components are capacitors, and the parameter with the first finite value and the parameter with the second finite value is capacitance.

14. An electrosurgical system according to claim 1, wherein the first unit is an electrosurgical generator and the second unit is an electrosurgical instrument detachably connected to the generator.

15. An electrosurgical system according to claim 1, wherein the first unit is a handheld electrosurgical handpiece and the second unit is an electrode unit detachably connected to the electrosurgical handpiece.

16. A method of operating an electrosurgical system comprising at least a first unit and a second unit, the second unit being detachably connectible to the first unit and being associated with an electrode assembly, the method comprising, whilst the second unit is connected to the first unit:

presenting from the second unit to the first unit, in a time-varying manner, a parameter with a first finite non-zero value for a first time period, and a parameter with a second finite value for a second time period;

detecting the parameters in the first unit;

providing an RF output signal from the first unit to the second unit; and adjusting the RF output signal of the first unit in response to the detection so as to suit the particular electrode assembly;

wherein the time-varying nature of providing the parameters provides for identification of the particular electrode assembly.

* * * * *